United States Patent
Timmins et al.

(10) Patent No.: US 11,331,284 B2
(45) Date of Patent: *May 17, 2022

(54) ISOTOPE ENHANCED AMBROXOL FOR LONG LASTING AUTOPHAGY INDUCTION

(71) Applicant: UNM Rainforest Innovations, Albuquerque, NM (US)

(72) Inventors: Graham Timmins, Albuquerque, NM (US); Vojo P. Deretic, Placitas, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/778,220

(22) Filed: Jan. 31, 2020

(65) Prior Publication Data

US 2020/0237687 A1 Jul. 30, 2020

Related U.S. Application Data

(63) Continuation of application No. 16/412,017, filed on May 14, 2019, now Pat. No. 10,583,099, which is a continuation of application No. PCT/US2018/016573, filed on Feb. 2, 2018.

(60) Provisional application No. 62/455,822, filed on Feb. 7, 2017.

(51) Int. Cl.
| | |
|---|---|
| *A61K 31/137* | (2006.01) |
| *A61P 11/00* | (2006.01) |
| *A61P 31/06* | (2006.01) |
| *A61K 31/136* | (2006.01) |
| *A61K 51/04* | (2006.01) |
| *A61K 35/00* | (2006.01) |
| *C07C 213/08* | (2006.01) |
| *A61K 31/395* | (2006.01) |
| *A61K 9/00* | (2006.01) |
| *C07C 215/42* | (2006.01) |
| *C07B 59/00* | (2006.01) |
| *A61P 31/04* | (2006.01) |
| *C07C 215/68* | (2006.01) |
| *A61K 45/06* | (2006.01) |
| *A61K 45/00* | (2006.01) |

(52) U.S. Cl.
CPC .......... *A61K 31/137* (2013.01); *A61K 9/0075* (2013.01); *A61K 31/136* (2013.01); *A61K 31/395* (2013.01); *A61K 35/00* (2013.01); *A61K 45/06* (2013.01); *A61K 51/0402* (2013.01); *A61P 11/00* (2018.01); *A61P 31/04* (2018.01); *A61P 31/06* (2018.01); *C07B 59/001* (2013.01); *C07C 213/08* (2013.01); *C07C 215/42* (2013.01); *C07C 215/68* (2013.01); *A61K 45/00* (2013.01)

(58) Field of Classification Search
None
See application file for complete search history.

(56) References Cited

PUBLICATIONS

Latli et al. Synthesis of labeled ambroxol and its major metabolites. 2010 J. Label. Compd. Radiopharm. 53: 15-23. (Year: 2010).*
Choi SW, et al.; Ambroxol induces autophagy and potentiates rifampicin antimicrobial activity. Antimicrobial Agents and Chemotherapy Sep. 2018; vol. 62, nr. 9, pp. e01019-18.
Deretic V, et al.; Enhancement of lung levels of antibiotics by ambroxol and bromhexine. Expert Opinion on Drug Metabolism & Toxicology Feb. 7, 2019; vol. 15, nr. 3, pp. 213-218.
Timmins GS et al.; Deuterated drugs: where are we now?; Expert Opin Ther Pat. Oct. 2014; vol. 24, nr. 10, pp. 1067-1075.
Timmins GS; Deuterated drugs: updates and obviousness analysis. Expert Opinion in Therapeutic Patents. 2017, vol. 27, nr. 12, pp. 1353-1361.
Timmins GT et al.; Nitric oxide generatedfrom Isoniazid activation by KatG: Source of nitric oxide and activity against *Mycobacterium tuberculosis*. Antiicrobial Agents and Chemotherapy. Aug. 2004; vol. 48, nr. 8, pp. 3006-3009.
Master SS et al.; *Mycobacterium tuberculosis* prevents inflammasome activation. Cell Host & Microbe. Apr. 2008; vol. 3, pp. 224-232.
Miller BH, et al.; Mycobacteria inhibit nitric oxide synthase recruitment to phagosomes during macrophage infection. Infection and Immunity. May 2004; vol. 72, nr. 5, pp. 2872-2878.

(Continued)

*Primary Examiner* — Jennifer Lamberski
(74) *Attorney, Agent, or Firm* — Henry D. Coleman; R. Neil Sudol (57) ABSTRACT

The present invention is directed to $^{13}$C and/or $^{2}$H isotope enhanced ambroxol ("isotope enhanced ambroxol") and its use in the treatment of autophagy infections, especially mycobacterial and other infections, disease states and/or conditions of the lung, such as tuberculosis, especially including drug resistant and multiple drug resistant tuberculosis. Pharmaceutical compositions comprising isotope enhanced ambroxol, alone or in combination with an additional bioactive agent are useful against an autophagy mediated disease state and/or condition, for example, a *Mycobacterium* infection, Chronic Obstructive Pulmonary Disease (COPD), asthma, pulmonary fibrosis, cystic fibrosis, Sjogren's disease and lung cancer. Methods of treating autophagy disease states and/or conditions, especially including autophagy disease states or conditions which occur principally in the lungs of a patient represent a further embodiment of the present invention. Methods of synthesizing compounds according to the present invention are disclosed herein.

14 Claims, 7 Drawing Sheets

(56) References Cited

PUBLICATIONS

Timmins GS, et al.; Requirements for nitric oxide generation from isoniazid activation in vitro and inhibition of Mycobacterial respiration in vivo. Journal of Bacteriology. Aug. 2004; vol. 186, nr. 16, pp. 5427-5431.

Pagan-Ramos E, et al.; Molecular and physiological effects of MycobacterialoxyR inactivation. Journal of Bacteriology. Apr. 2006; vol. 188, nr. 7, pp. 2674-2680.

Maiga M, et al.; Stool microbiome reveals diverse bacterial ureases as confounders of oral urea breath testing foe Helicobacter pylori and *Mycobacterium tuberculosis* in Bamako, Mali. Journal of Breath Research. Aug. 17, 2016; vol. 10, 036012.

Jain P, et al.; Reporter phage and breath tests: Emerging phenotypic assays for diagnosing active tuberculosis, antibiotic resistance, and treatment efficacy. The Journal of Infectious Diseases. 2011; vol. 204, (Suppl 4), pp. S1142-S1150.

Deretic V, et al.; Immunologic manifestations of autophagy. J Clin Invest. 2015; vol. 125, nr. 1, pp. 75-84.

Maiga M, et al.; In vitro and in vivo studies of a rapid and selective breath test for tuberculosis based upon Mycobacterial CO dehydrogenase. mBio 2014; vol. 5, nr. 2:, pp. e00990-14.

Master SS et al.; Oxidative stress response genes in *Mycobacterium tuberculosis*: role of ahpC in resistance to peroxynitrate and stage-specific survival in macrophages. Microbiology (GB) 2002; vol. 148, pp. 3139-3144.

Timmins GS et al.; Mechanisms of action of isoniazid. Molecular Microbiology 2006; vol. 62, nr. 5, pp. 1220-1227.

Choi SW, et al.; Rapid in vivo detection of isoniazid-sensitive *Mycobacterium tuberculosis* by breath test. Nature Communications Sep. 23, 2014; vol. 5, pp. 4989.

Jassal MS, et al.; 13[C]-Urea breath test as a novel point-of-care biomarker for tuberculosis treatment and diagnosis. PLoS One Aug. 27, 2010; vol. 5, nr. 8: e12451.

Castillo EF, et al.; Autophagy protects against active tuberculosis by suppressing bacterial burden and inflammation. Proc. Natl Acad. Sci (US) Oct. 23, 2012; vol. 109, nr. 46, e3168-3176.

Timmins GS; Detecting virulence and drug-resistance mycobacterial phenotypes in vivo. Trends in Microbiology Jun. 2015; vol. 23, nr. 6, pp. 321-323.

Chauhan S, et al.;Pharmaceutical screen identifies novel target processes for activation of autophagy with aq broad translational potential. Nature Communications Oct. 27, 2015.

Avison, et al. Applications of NMR to studies of tissue metabolism. Ann Rev Biophys, Biophys Chem, 1986;15:377-402.

\* cited by examiner

ISOTOPE ENHANCED AMBROXOL FOR LONG LASTING AUTOPHAGY INDUCTION

RELATED APPLICATIONS

The present application is a continuation application of U.S. patent application Ser. No. 16/411,017, now U. S. Pat. No. 10,583,099, which issued Mar. 10, 2020, which itself is a continuation application of international application number PCT/US2018/016,673 of international filing date. Feb. 2, 2018, which claims the benefit of priority of U.S. provisional application Ser. No. 62/455,822 filed Feb. 7, 2017 of identical title, the entire contents of all of said applications being incorporated herein.

FIELD OF THE INVENTION

The present invention is directed to $^{13}$C and or $^2$H isotope enhanced ambroxol ("isotope enhanced ambroxol") and its use in the treatment of autophagy infections, especially mycobacterial infections of the lung, such as *tuberculosis*, especially including drug resistant and multiple drug resistant *tuberculosis*, and also including a range of rifampin sensitive lung, infections such as pneumonias caused by methicillin resistant *Staphylococcus aureus* (MRSA) carbapenem-resistant *Acinetobacter baumannii*, and inhalational anthrax (caused by *Bacillus anthracis*). Pharmaceutical compositions comprising isotope enhanced ambroxol, alone or in combination with an additional bioactive agent, including an additional autophagy modulator (an agent which is active to promote or inhibit autophagy), thus being useful against an autophagy mediated disease state and/or condition), especially an autophagy mediated disease state and/or condition which occurs in the lungs, for example, a *Mycobacterium* infection, a non-*Mycobacterium* lung infection, Chronic Obstructive Pulmonary Disease (COPD), asthma, pulmonary fibrosis, cystic fibrosis, Sjogren's disease and lung cancer (especially small cell and non-small cell lung cancer). Methods of treating autophagy disease states and/or conditions, especially including autophagy disease states or conditions which occur principally in the lungs of a patient represent a further embodiment of the present invention. An additional embodiment includes methods of synthesizing compounds according to the present invention as otherwise disclosed herein.

BACKGROUND AND OVERVIEW OF THE INVENTION

Unpublished data from the inventors evidences that Ambroxol is a powerful inducer of autophagy. However, its plasma half-life in humans is only 3.72 hours (1) meaning multiple doses daily need to be given in order to provide an effective concentration. Its major route of elimination is via urinary excretion of a glucuronide (2) conjugate, so any other factors are not predicted to alter metabolism or tissue. pharmacokinetics or dynamics.

Figure 1:
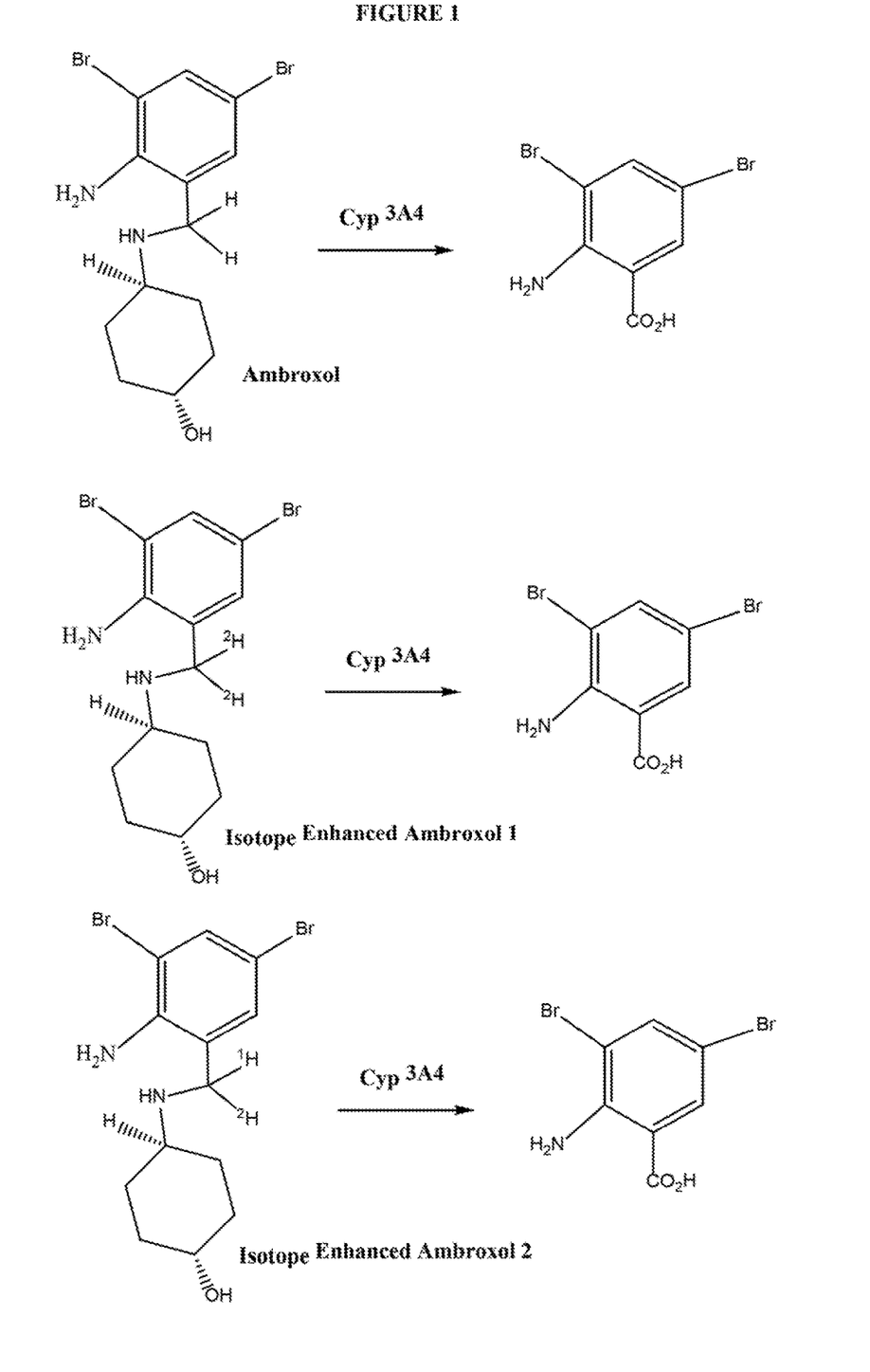

Ambroxol's major metabolism by human microsomes was shown to be by cyp3A4 mediated oxidation to dibromoanthranilic acid (DBAA). (3) See FIG. 1. Thus, any potential use of ambroxol in treating diseases autophagy-mediated disease states and/or conditions like *tuberculosis* (TB) may be greatly compromised by the cyp3A4 inducing nature of many TB medicines such as rifampin. Alternatively, the use of cyp3A4 inhibiting medications with ambroxol may also lead to greater than desired levels of ambroxol because it is no longer being metabolized by cyp3A4. Thus, unfortunately, the inherent susceptibility of ambroxol to cyp3A4 will make it difficult to dose in humans in diseases such as TB treated, with rifampin or other anti-TB agents, or when cyp3A4 inhibiting compounds are given.

Furthermore, ambroxol displays lung concentrating effects that will potentiate its effects in lung diseases such as *tuberculosis*. It is rarely acknowledged that lung tissues express significant cyp3A4, as well as the more commonly understood liver expression, and cyp3A4 is found in human lungs in sites including bronchial glands, bronchiolar columnar and terminal epithelium, type II alveolar epithelium, and alveolar macrophages. (4) Therefore, even if ambroxol is given in inhaled forms, it will inherently and unexpectedly be metabolized into inactive forms by lung tissue cyp3A4 limiting lung exposure levels to ambroxol.

BRIEF DESCRIPTION OF THE INVENTION

In one embodiment, the inventors disclose isotope enhanced forms of ambroxol (isotope enhanced ambroxol 1 through 4—see attached FIG. 1) that will resist cyp3A4 metabolism. This series of compounds will allow more optimal use of ambroxol, especially orally or inhaled, and will be inherently unexpected alterations in plasma or a tissue levels from cyp3A4 presence, induction or inhibition.

According, to the present invention, the following isotopes $^{13}$C and/or $^2$H isotopes of ambroxol are provided, Thus, a first embodiment is directed to isotopically labeled compounds according to the chemical formula:

-continued

[Chemical structure: dibromo aminophenyl compound with $^{13}C$-labeled methylene ($^1H$, $^1H$), HN linked to cyclohexanol with OH]

or a pharmaceutically acceptable salt, stereoisomer (including a diastereomer and/or enantiomer), solvate or polymorph thereof.

In another embodiment, the present invention is directed to pharmaceutical compositions comprising an effective amount of at least one isotopically labeled ambroxol compound as described above, in combination with a pharmaceutically acceptable additive, carrier and/or excipient. Pharmaceutical compositions described above may be optionally combined with at least one additional bioactive agent, preferably an anticancer agent (preferably an anticancer agent effective to treat lung cancer, including small cell lung cancer and non-small cell lung cancer such as Cisplatin, Carboplatin, Paclitaxel (Taxol), Albumin-bound paclitaxel nab-paclitaxel, Abraxane), Docetaxel (Taxotere), Gemcitabine (Gemzar), Vinorelbine (Navelbine), Irinotecan (Camptosar), Etoposide (VP-16), Vinblastine, Pemetrexed (Alimta) and mixtures thereof), or an agent which is useful in the treatment of a mycobacterial infection, especially including a *tuberculosis* infection or another autophagy mediated disease. In certain embodiments, the additional bioactive agent is an anti-*tuberculosis* agents such as ethambutol, isoniazid, ethionamide, prothionamide, pyrazinamide, rifampacin or mixtures thereof. In other embodiments, the additional bioactive agent is an autophagy modulator as otherwise described herein. In still other embodiments, the additional bioactive agent may include both an anti-*tuberculosis* agent and/or an additional autophagy modulator as described herein. In still other embodiments the bioactive agent is or includes rifampin and other rifamycin derivatives such as rifabutin, rifamixin and rifapentine are vitally important drugs in regimens for non-tuberculous mycobacteria lung (NTM) infections such as *Mycobacterium avium* complex MAC) and *M. kansasii*.

In another embodiment, the present invention is directed to a method for treating an autophagy-mediated disease state or condition in a patient, especially including an autophagy-mediated disease state or condition principally localized in the lungs of a patient, comprising administering an effective amount of at least one isotopically labeled ambroxol compound to a patient in need, optimally in combination with at least one additional bioactive agent, which, bioactive agent may include an anti-*tuberculosis* agent and/or an autophagy modulator. While any number of autophagy mediated disease states and/or conditions may be treated using compounds and optional agents according to the present invention, in preferred embodiments, the present methods are directed to the treatment of diseases which are principally found in the lungs of a patient. The disease states and/or conditions of the lung which may be treated pursuant to the present in invention include, for example, a *Mycobacterium* infection (especially including *tuberculosis*) but including other infections such as tuberculous and non-tuberculous mycobacteria (such as *M. kansasii, M. avium* and *M. abscessus*), non-mycobacterial lung infections, such as pneumonias caused by methicillin resistant *Staphylococcus aureus* (MRSA), carbapenem-resistant *Acinetobacter baumannii*, and inhalational anthrax, Chronic Obstructive Pulmonary Disease (COPD), asthma, pulmonary fibrosis, cystic fibrosis, Sjogren's disease and lung cancer (small cell and non-small cell lung cancer). In still other embodiments the bioactive agent is or includes rifampin and other rifamycin derivatives such as rifabutin, rifamixin and rifapentine which are vitally important drugs in regimens for non-tuberculous mycobacteria lung (NTM) infections such as *Mycobacterium avium* complex (MAC), *M. kansasii* and *M. abscessus*. For TB, standard 'short' course therapy includes 6 months therapy with rifampin. In NTM therapy even longer treatment courses are required. For MAC, the drug treatment cessation is only recommended after 12 months of sputum culture negativity (SCN), so treatments greatly in excess of 1 year are common. The recommendations for *M. kansasii* are also for 20 months therapy with at least 12 months of therapy after SCN is achieved. These are very long treatment courses compared to most bacterial disease, and their treatment can be meaningfully improved and therapy times shortened by rifamycin derivatives such as rifampin, rifabutin, rifamixin and rifapentine (preferably rifampin) potentiation by the agents described herein.

In another embodiment, isotopically enhanced ambroxol can potentiate rifampin and other rifamycin derivatives such as rifabutin, rifamixin and rifapentine, alone or in mixtures thereof for treating non-mycobacterial lung infections, such as pneumonias caused by methicillin resistant *Staphylococcus aureus* (MRSA), carbapenem-resistant *Acinetobacter baumannii*, and inhalational anthrax, the method comprising administering an effective amount of one or more of the above agents to a patient in need of therapy thereof.

In another embodiment, the present invention is directed to a method of improving the pharmacokinetics and/or bioavailability of ambroxol in a patient after administration comprising administering an isotopically labeled ambroxol compound as described herein to a patient in need.

Figure 2:
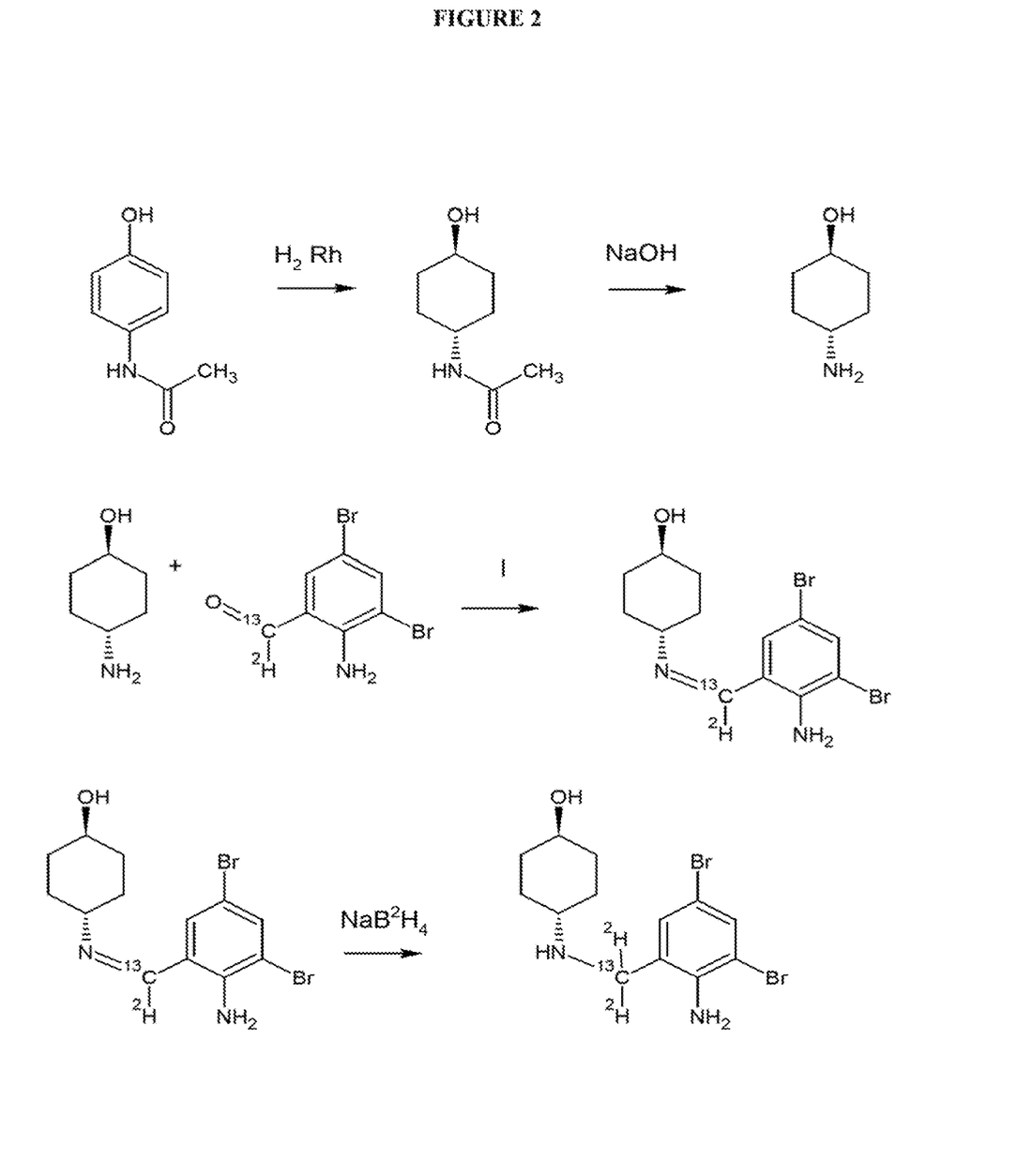
FIG. 2, scheme 1, provides a synthetic scheme for producing isotopically-labeled ambroxol compounds according to the present invention. In this method an enantiomerically enriched 1-hydroxy-4-aminocyclohexane is reacted with an isotopically enriched dibromoaminobenzaldehyde as indicated. The imine which is formed is then subjected to reduction using an isotopically labeled reducing agent to provide the final isotopically labeled ambroxol. Various iterations of the compounds according to the present invention are readily produced by varying the atom which is isotopically labeled in the dibromoaminobenzaldehyde compound or the reducing agent.

In yet another embodiment, the present invention is directed to a method of synthesizing isotopically labeled ambroxol, the method comprising (as depicted in FIG. 2 hereof) reacting 4 amino cyclohexanol of depicted configuration (FIG. 2) with an isotopically labeled dibromo amino benzaldehyde to provide the isotopically labeled imine (FIG. 2) which is further reduced to provide one or more of the isotopically labeled compounds according to the present invention.

BRIEF DESCRIPTION OF THE FIGURES

FIG. 1 shows the various isotopically labeled ambroxol derivatives according to the present invention. Compounds which are exhibited in FIG. 1 include trans-4-[(2-amino-3,5-dibromobenzyl)amino]cyclohexanol (ambroxol), trans-4-{[(2-amino-3,5-dibromobenzyl)($^2H_1$, $^1H_1$)methyl]amino]cyclohexanol (isotope enhanced ambroxol 1), trans-4-{[(2-amino-3,5-dibromobenzyl)($^2H_2$)-methyl]amino]cyclohexanol (isotope enhanced ambroxol 2), trans-4-{[(2-amino-3,5-dibromobenzyl)($^2H_2$, $^{13}C$)methyl]amino]cyclohexanol (isotope enhanced ambroxol 3) and trans-4-{[(2-amino-3,5-dibromobenzyl)($^2H_1$, $^1H_1$, $^{13}C$)methyl]amino]cyclohexanol (isotope enhanced ambroxol 4) The isotopic ambroxol compounds are resistant to Cyp3A4 metabolism. This figure shows ambroxol and the isotopic forms 1-4 and how they will resist cyp3A4 metabolism.

FIG. 3 shows the dose response of wild type cells. This figure clearly shows that even concentrations as low as 6.25 μM had a positive effects on autophagy (t test v. control p 0.025). The data show that across the range of ambroxol concentrations from 0 to 200 μM, higher ambroxol concentrations result in higher induction of autophagy.

DETAILED DESCRIPTION OF THE INVENTION

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items. It is noted that when a range is described in the specification, every single integer falling within the range is also included within the range, unless the context of the use of the range specifically excludes an integer within that range.

The term "compound" or "agent", as used herein, unless otherwise indicated, refers to any specific chemical compound disclosed herein, especially including ambroxol or a derivative thereof or other autophagy modulator and includes tautomers, regioisomers, geometric isomers as applicable, and also where applicable, optical isomers (e.g. enantiomers) thereof, as well as pharmaceutically acceptable salts thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds as well as diastereomers and epimers, where applicable in context. The term also refers, in context to prodrug forms of compounds which have been modified to facilitate the administration and delivery of compounds to a site of activity.

The term "patient" or "subject" is used throughout the specification within context to describe an animal, generally a mammal, including a domesticated mammal including a farm animal (dog cat, horse, cow pin, sheep, goat, etc.) and preferably a human, to whom treatment, including prophylactic treatment (prophylaxis), with the methods and compositions according to the present invention is provided. For treatment of those conditions or disease states which are specific for a specific animal such as a human patient, the term patient refers to that specific animal, often a human.

The terms "effective" or "pharmaceutically effective" are used herein, unless otherwise indicated, to describe an amount of a compound or composition which, in context, is used to produce or affect an intended result, usually the modulation of autophagy within the context of a particular treatment in the lungs of a patient or subject.

The terms "treat", "treating", and "treatment", etc., as used herein, refer to any action providing a benefit to a patient at risk for or afflicted by an autophagy mediated disease state or condition as otherwise described herein. The benefit may be in curing the disease state or condition, inhibition its progression, or ameliorating, lessening or suppressing one or more symptom of an autophagy mediated disease state or condition. Treatment, as used herein, encompasses both prophylactic and therapeutic treatment.

As used herein, the term "autophagy mediated disease state or condition" or an "autophagy mediated lung disease" refers to a disease state or condition that results from disruption in autophagy or cellular self-digestion and occurs in the lung of a patient or subject. Autophagy is a cellular pathway involved in protein and organelle degradation, and has a large number of connections to human disease. Autophagic dysfunction is associated with cancer, neurodegeneration, microbial infection and ageing, among numerous other disease states and/or conditions. Although autophagy plays a principal role as a protective process for the cell, it also plays a role in cell death. Disease states and/or conditions which are mediated through autophagy (which refers to the fact that the disease state or condition may manifest itself as a function of the increase or decrease in autophagy in the patient or subject to be treated and treatment requires administration of an inhibitor or agonist of autophagy in the patient or subject.

Disease states and/or conditions which are mediated through autophagy (which refers to the fact that the disease state or condition may manifest itself as a function of the increase or decrease in autophagy in the patient or subject to be treated and treatment requires administration of an inhibitor or agonist of autophagy in the patient or subject) include, for example, cancer, including metastasis of cancer, lysosomal storage diseases (discussed herein below), neurodegeneration (including, for example, Alzheimer's disease. Parkinson's disease, Huntington's disease; other ataxias), immune response (T cell maturation, B cell and T cell homeostasis, counters damaging inflammation) and chronic inflammatory diseases (may promote excessive cytokines when autophagy is defective), including, for example, inflammatory bowel disease, including Crohn's disease, rheumatoid arthritis, lupus, multiple sclerosis, chronic obstructive pulmonary disease/COPD, pulmonary fibrosis, cystic fibrosis, Sjogren's disease; hyperglycemic disorders, diabetes (I and II), affecting lipid metabolism islet function and/or structure, excessive autophagy may lead to pancreatic β-cell death and related hyperglycemic disorders, including severe insulin resistance, hyperinsulinemia insulin-resistant diabetes (e.g. Mendenhall's Syndrome, Werner Syndrome, leprechaunism, and lipoatrophic diabetes) and dyslipidemia (e.g. hyperlipidemia as expressed by obese subjects, elevated low-density lipoprotein (LDL), depressed high-density lipoprotein (HDL), and elevated triglycerides and metabolic syndrome, liver disease (excessive autophagic removal of cellular entities-endoplasmic reticulum), renal disease (apoptosis in plaques, glomerular disease), cardiovascular disease (especially including ischemia, stroke, pressure overload and complications during reperfusion), muscle degeneration and atrophy, symptoms of aging (including amelioration or the delay in onset or severity or frequency of aging-related symptoms and chronic conditions including muscle atrophy, frailty, metabolic disorders, low grade inflammation, atherosclerosis and associated conditions such as cardiac and neurological both central and peripheral manifestations including stroke, age-associated dementia and sporadic form of Alzheimer's disease, precancerous states, and psychiatric conditions including depression), stroke and spinal cord injury, arteriosclerosis, infectious diseases (microbial infections, removes microbes, provides a protective inflammatory response to microbial products, limits adaptation of autophagy of host by microbe for enhancement of microbial growth, regulation of innate immunity) including bacterial, fungal, cellular and viral (including secondary disease states or conditions associated with infectious diseases), including AIDS and *tuberculosis*, among others, development (including erythrocyte differentiation), embryogenesis/fertility/infertility (embryo implantation and neonate survival after termination of transplacental supply of nutrients, removal of dead cells during programmed cell death) and ageing (increased autophagy leads to the removal of damaged organelles or aggregated macromolecules to increase health and prolong lire, but increased levels of autophagy in children/young adults may lead to muscle and organ wasting resulting in ageing/progeria).

The term "lysosomal storage disorder" refers to disease state or condition that results from a defect in lysosomal storage. These disease states or conditions generally occur when the lysosome malfunctions. Lysosomal storage disorders are caused by lysosomal dysfunction usually as a consequence of deficiency of a single enzyme required for the metabolism of lipids, glycoproteins or mucopolysaccharides. The incidence of lysosomal storage disorder (collectively) occurs at an incidence of about 1:5,000-1:10,000. The lysosome is commonly referred to as the cell's recycling center because it processes unwanted material into substances that the cell can utilize. Lysosomes break down this unwanted matter via high specialized enzymes. Lysosomal disorders generally are triggered when a particular enzyme exists in too small an amount or is missing altogether. When this happens, substances accumulate in the cell. In other words, when the lysosome doesn't function normally, excess products destined for breakdown and recycling are stored in the cell. Lysosomal storage disorders are genetic diseases, but these may be treated using autophagy modulators (autostatins) as described herein. All of these diseases share a common biochemical characteristic, i.e. that all lysosomal disorders originate from an abnormal accumulation of substances inside the lysosome. Lysosomal storage diseases mostly affect children who often die as a consequence at an early stage of life, many within a few months or years of birth. Many other children die of this disease following years of suffering from various symptoms of their particular disorder.

Examples of lysosomal storage diseases include, for example, activator deficiency/GM2 gangliosidosis, alpha-mannosidosis, aspartylglucoaminuria, cholesteryl ester, storage disease, chronic hexosaminidase A deficiency, cystinosis, Danon disease, Fabry disease, Farber disease, fucosidosis, galactosialidosis, Gaucher Disease (Types I, II and III), GM! Gangliosidosis, including infantile, late infantile/juvenile and adult/chronic), Hunter syndrome (MPS II), I-Cell disease/Mucolipidosis II, Infantile Free Sialic Acid Storage Disease (ISSD), Juvenile Hexosaminidase A Deficiency, Krabbe disease, Lysosomal acid lipase deficiency, Metachromatic Leukodystrophy, Hurler syndrome, Scheie syndrome, Hurler-Scheie syndrome, Sanfilippo syndrome, Morquio Type A and B, Maroteaux-Lamy, Sly syndrome, mucolipidosis, multiple sulfate deficiency, Niemann-Pick disease, Neuronal ceroid lipofuscinosis, CLN6 disease, Jansky-Bielschowsky disease, Pompe disease, pycnodysostosis, Sandhoff disease, Schindler disease, Tay-Sachs and Wolman disease, among others.

In preferred aspects, isotopically labeled ambroxol is used often to treat autophagy-mediated lung diseases, such as *Mycobacterium* infections including non-*tuberculosis* and *tuberculosis*, Chronic Obstructive Pulmonary Disease (COPD), asthma, pulmonary fibrosis, cystic fibrosis, Sjogren's disease and lung cancer (small cell and non-small cell lung cancer) Isotopically enhanced ambroxol can also potentiate rifampin and other rifamycin derivatives such as rifabutin, rifamixin and rifapentine, alone or in mixtures thereof for treating non-mycobacterial lung infections, such as pneumonias caused by methicillin resistant *Staphylococcus aureus* (MRSA), carbapenem-resistant *Acinetobacter baumannii*, and inhalational anthrax.

Additional autophagy modulators (which may be coadministered with isotopically labeled ambroxol) also it Astemizole, Chrysophanol, Emetine, Chlorosalicylanilide, Oxiconazole, Sibutramine, Proadifen, Dihydroergotamine tartrate, Terfenadine, Triflupromazine, Amiodarone, Saponin Vinblastine, Tannic acid, Fenticlor, Pizotyline malate, Piperacetazine, Oxyphencyclimine, Glyburide, Hydroxychloroquine, Methotrimeprazine, Mepartricin, Thiamylal Sodium Triclocarban, Diphenidol, Karanjin, Clovanediol diacetate, Nerolidol, Fluoxetine, Helenine, Dehydroabietamide, Dibutyl Phthalate, 18-aminoabieta-8, 11, 13-triene sulfate, Podophyllin acetate, Berbamine, Rotenone, Rubescensin A, Morin, Pyrromycin, Pomiferin, Gardenin A, alpha-mangostin, Avocadene, Butylated hydroxytoluene, Physcion, Tetrandrine, Malathion, Isoliquiritigenin, Clofoctol, Isoreserpine, 4,4'-dimethoxydalbergione and 4-methyldaphnetin, and mixtures thereof. Other agents which may be coadministered with ambroxol, include benzethonium, niclosamide, monensin, bromperidol, levobunolol, dehydroisoandrosterone 3-acetate, flubendazole, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepine, biperiden, denatonium, etomidate, toremifene, tomoxetine, clorgyline, zotepine, beta-escin, tridihexethyl, ceftazidime, methoxy-6-harmalane, melengestrol, albendazole, rimantadine, chlorpromazine, pergolide, cloperastine, prednicarbate, haloperidol, clotrimazole, nitrofural iopanoic acid, naftopidil, Methimazole, Trimeprazine, Ethoxyquin, Clocortolone, Doxycycline, Pirlindole mesylate, Doxazosin, Deptropine, Nocodazole, Scopolamine, Oxybenzone, Halcinonide, Oxybutynin, Miconazole, Clomipramine, Cyproheptadine, Doxepin, Dyclonine, Salbutamol, Flavoxate, Amoxapine, Fenofibrate, Pimethixene or a pharmaceutically acceptable salt, alternative salt and mixtures thereof. One or more of these agents may be formulated in inhalation/pulmonary dosage form, but often these agents are simply coadministered with ambroxol via other routes of administration (ie, oral, parenteral, etc.).

Other agents which may be co-administered with ambroxol include anti-*tuberculosis* agents, for example ethambutol, isoniazid, ethionamide, propionamide, pyrazinamide, rifampicin, aminosalicylic acid, bedaquiline, rifabutin, rifapentine, capreomycin, cycloserine and mixtures thereof. The use of ethambutol, isoniazid, ethionamide, propionamide, pyrazinamide, rifampicin and mixtures thereof are preferred.

The term "co-administration" or "combination therapy" is used to describe a therapy in which at least two active compounds in effective amounts are used to treat an autophagy mediated disease state or condition as otherwise described herein, either at the same time or within dosing or administration schedules defined further herein or ascertainable by those of ordinary skill in the art. The two compounds may be administered in the same composition. Although the term co-administration preferably includes the administration of two active compounds to the patient at the same time, it is not necessary that the compounds be administered to the patient at the same time, although effective amounts of the individual compounds will be present in the patient at the same time. In addition, in certain embodiments, co-administration will refer to the fact that two compounds are administered at significantly different times, but the effects of the two compounds are present at the same time. Thus, the term co-administration includes art administration where ambroxol is coadministered with at least one additional active agent (including another autophagy modulator) at approximately the same time (contemporaneously), or from about one to several minutes to about 24 hours or more before or after the other bioactive agent is administered. The additional bioactive agent may be any bioactive agent, but is often an additional autophagy mediated compound which serves to enhance the activity of isotopically labeled ambroxol or one of its derivatives.

The present invention includes compositions comprising the pharmaceutically acceptable salt. i.e., the acid or base addition salts of compounds of the present invention and their derivatives. The acids which may be used to prepare the pharmaceutically acceptable acid addition salts of the aforementioned base compounds useful in this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate]salts, among others.

Pharmaceutically acceptable base addition salts may also be used to produce pharmaceutically acceptable salt forms of the compounds according to the present invention. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (e, calcium and magnesium), ammonium or water-soluble amine addition salts such as N-methylglucamine-(meglumine), and the lower alkanolammonium and other base salts of pharmaceutically acceptable organic amines, among others.

As indicated, the pharmaceutical composition may comprise, in addition to at least one isotopically labeled ambroxol and optional bioactive agent, including an autophagy modulator, a pharmaceutically acceptable excipient, additive or inert carrier. The pharmaceutically acceptable excipient, additive or inert carrier may be in a form chosen from a solid, semi-solid, and liquid. The pharmaceutically acceptable excipient or additive may be chosen from a starch, crystalline cellulose, sodium starch glycolate, polyvinylpyrolidone, polyvinylpolypyrrolidone, sodium acetate, magnesium stearate, sodium laurylsulfate, sucrose, gelatin, silicic acid, polyethylene glycol, water, alcohol, propylene glycol, vegetable oil, corn oil, peanut oil, olive oil, surfactants, lubricants, disintegrating agents, preservative agents, flavoring agents, pigments, and other conventional additives. The pharmaceutical composition may be formulated by admixing the active with a pharmaceutically acceptable excipient or additive.

The pharmaceutical composition may be in a form chosen from sterile isotonic aqueous solutions, pills, drops, pastes, cream, spray (including aerosols), capsules, tablets, sugar coating tablets, granules, suppositories, liquid, lotion, suspension, emulsion, ointment, gel, and the like. Administration route may be chosen from subcutaneous, intravenous, intestinal, parenteral, oral, buccal, nasal, intramuscular, transcutaneous, transdermal, intranasal, intratracheal, intrapulmonary, intraperitoneal, and topical. The pharmaceutical compositions may be immediate release, sustained/controlled release, or a combination of immediate release and sustained/controlled release depending upon the compound(s) to be delivered, the compound(s), if any, to be coadministered, as well as the disease state and/or condition to be treated with the pharmaceutical composition. A pharmaceutical composition may be formulated with differing compartments or layers in order to facilitate effective administration of any variety consistent with good pharmaceutical practice. Oral and inhalation dosage forms are preferred, especially for the treatment of disease states and/or conditions which are localized principally in the lungs of a patient.

The subject or patient may be chosen from, for example, a human, a mammal such as domesticated animal, or other animal. The subject may have one or more of the disease states, conditions or symptoms associated with autophagy as otherwise described herein.

The compounds according to the present invention may be administered in an effective amount to treat or reduce the likelihood of an autophagy-mediated disease and/or condition as well one or more symptoms associated with the disease state or condition. One of ordinary skill in the art would be readily able to determine an effective amount of active ingredient by taking into consideration several variables including, but not limited to, the animal subject, age, sex, weight, site of the disease state or condition in the patient, previous medical history, other medications, etc.

For example, the dose of an active ingredient which is useful in the treatment of an autophagy mediated disease state, condition and/or symptom for a human patient is that which is an effective amount and may range from as little as 50-100 µg or even less to at least about 500 mg or more (up to several grams or more) per day, which may be administered in a manner consistent with the delivery of the drug and the disease state or condition to be treated. In the case of oral administration, active is generally administered from one to four times or more daily. Transdermal patches or other topical administration may administer drugs continuously, one or more times a day or less frequently than daily, depending upon the absorptivity of the active and delivery to the patient's skin. Of course, in certain instances where parenteral administration represents a favorable treatment option, intramuscular administration or slow IV drip may be used to administer active. The amount of active ingredient which is administered to a human patient preferably ranges from about 0.05 mg/kg to about 25 mg/leg, about 0.1 mg/kg to about 10 mg/kg, about 0.25 mg/kg to about 7.5 mg/kg., about 1.25 to about 5.7 mg/kg.

The dose of a compound according to the present invention may be administered at the first signs of the onset of an autophagy mediated disease state, condition or symptom. For example, the dose may be administered for the purpose of lung or heart function and/or treating or reducing the likelihood of any one or more of the disease states or conditions which become manifest during an inflammation-associated metabolic disorder or *tuberculosis* or associated disease states or conditions, including pain, high blood pressure, renal failure, or lung failure. The dose of active ingredient may be administered at the first sign of relevant symptoms prior to diagnosis, but in anticipation of the disease or disorder or in anticipation of decreased bodily function or any one or more of the other symptoms or secondary disease states or conditions associated with an autophagy mediated disorder to condition.

In preferred aspects of the invention, isotopically labeled ambroxol is administered to the patient or subject often by oral administration or even more often to the lungs of the patient or subject often via pulmonary administration, including intratracheal administration. The pharmaceutical composition of the invention for pulmonary administration is usually used as an inhalant. The composition can be formed into dry powder inhalants, inhalant suspensions, inhalant solutions, encapsulated inhalants and like known forms of inhalants as described herein below. Such forms of inhalants can be prepared by filling the pharmaceutical composition of the invention into an appropriate inhaler such as a metered-dose inhaler, dry powder inhaler, atomizer bottle, nebulizer etc. before use. Of the above forms of inhalants, powder inhalants may be preferable, although nebulized suspensions and metered dose inhalers may also be used effectively.

When the pharmaceutical composition of the invention is used in the form of a powder, the mean particle diameter of the powder is not especially limited but, in view of the residence of the particles in the lungs, is preferable that the particles fall within the range of about 0.01 to 20 µm, often 0.05 to about 5 µm (to target both macrophages and lung epithelial cells), often about 0.05 to about 0.25 µm (to target lung epithelial cells), often about 1 to 3 µm (to target lung macrophages) and particularly about 1 to 5 µm, more often about 1 to 2 µm (microns). Although the particle size distribution of the powder pharmaceutical composition of the invention is not particularly limited, it is preferable that particles having a size of about 25 µm or more account for not more than about 5% of the particles, and preferably, 1% or less to maximize delivery into the lungs of the subject.

The pharmaceutical composition in the form of a powder of the invention can be produced by, for example, using the drying-micronization method, the spray drying method and standard pharmaceutical methodology well known in the art.

By way of example without limitation, according to the drying-pulverization method, the pharmaceutical composition in the form of a powder can be prepared drying an aqueous solution (or aqueous dispersion) containing the compound or mixtures with other active agents thereof and excipients which provide for immediate release in pulmonary tissue and microparticulating the dried product. Stated more specifically, after dissolving (or dispersing) a pharmaceutically acceptable carrier, additive or excipient in an aqueous medium, compounds according to the present invention in effective amounts are added and dissolved (or dispersed) by stirring using a homogenizer, etc. to give an aqueous solution (or aqueous dispersion). The aqueous medium may be water alone or a mixture of water and a lower alcohol. Examples of usable lower alcohols include methanol, ethanol, 1-propanol, 2-propanol and like water-miscible alcohols. Ethanol is particularly preferable. After the obtained aqueous solution (or aqueous dispersion) is dried by blower, lyophilization, etc., the resulting product is pulverized or microparticulated into fine particles using jet mills, ball mills or like devices to give a powder having the above mean particle diameter. If necessary, additives as mentioned above may be added in any of the above steps.

According to the spray-drying method, the pharmaceutical composition in the form of a powder of the invention can be prepared, for example, by spray-drying an aqueous solution (or aqueous dispersion) containing ambroxol and/or one or more ambroxol derivatives and optionally one or more additional agents such as an additional autophagy modulator as described herein and/or one or more anti-*tuberculosis* agent and excipients, additives and/or carriers for microparticulation. The aqueous solution (or aqueous dispersion) can be prepared following the procedure of the above drying-micronization method. The spray-drying process can be performed using a known method, thereby giving a powdery pharmaceutical composition in the form of globular particles with the above-mentioned mean particle diameter.

The inhalant suspensions, inhalant solutions, encapsulated inhalants, etc. can also be prepared using the pharmaceutical composition in the form of a powder produced by the drying-micronization method, the spray-drying method and the like, or by using a carrier, additive or excipient and isoniazid, urea or mixtures thereof that can be administered via the lungs, according to known preparation methods.

Furthermore, the inhalant comprising the pharmaceutical composition of the invention is preferably used as an aerosol. The aerosol can be prepared, for example, by filling the pharmaceutical composition of the invention and a propellant into an aerosol container. If necessary, dispersants, solvents and the like may be added. The aerosols may be prepared as 2-phase systems, 3-phase systems and diaphragm systems (double containers). The aerosol can be used in any form of a powder, suspension, solution or the like.

Examples of usable propellants include liquefied gas propellants, compressed gases and the like. Usable liquefied gas propellants include, for example, fluorinated hydrocarbons (e.g., CFC substitutes such as HCFC-22, HCFC-123, HFC-134a, HFC-227 and the like), liquefied petroleum, dimethyl ether and the like. Usable compressed gases include, for example, soluble gases (e.g., carbon dioxide, nitric oxide), insoluble gases (e.g., nitrogen) and the like.

The dispersant and solvent may be suitably selected from the additives mentioned above. The aerosol can be prepared, for example, by a known 2-step method comprising the step of preparing the composition of the invention and the step of filling and sealing the composition and propellant into the aerosol container.

As a preferred embodiment of the aerosol according to the invention, the following aerosol can be mentioned: Examples of the compounds to be used include isotopically labeled compound alone or in mixtures with other compounds according to the present invention or with other anti-Mycobacterial agents. As propellants, fluorinated hydrocarbons such as HFC-134a, HFC-227 and like CFC substitutes are preferable. Examples of usable solvents include water, ethanol, 2-propanol and the like. Water and ethanol are particularly preferable. In particular, a weight ratio of water to ethanol in the range of about 0:1 to 10:1 may be used.

The aerosol of the invention contains excipient in an amount ranging from about 0.01 to about $10^4$ wt. % (preferably about 0.1 to $10^3$ wt. %), propellant in an amount of about $10^2$ to $10^7$ wt. % (preferably about $10^3$ to $10^6$ wt. %), solvent in an amount of about 0 to $10^6$ wt. % (preferably about 10 to $10^5$ wt. %), and dispersant in an amount of 0 to $10^3$ wt. % (preferably about 0.01 to $10^2$ wt. %), relative to the weight of compound according to the present invention which is included in the final composition.

The pharmaceutical compositions of the invention are safe and effective for use in the therapeutic methods according to the present invention. Although the dosage of the composition of the invention may vary depending on the type of active substance administered (e.g. isotopically labeled ambroxol and optionally an additional autophagy modulating agent and/or anti-*tuberculosis* agent such as ethambutol, isoniazid, ethionamide, prothionamide, pyrazinamide, rifampacin, mixtures thereof and optional additional anti-*tuberculosis* agents) as well as the nature (size, weight, etc.) of the subject to be diagnosed, the composition is administered in an amount effective for treating any one or more of the lung diseases mediated through autophagy. For example, the composition is preferably administered such that the active ingredient (isotopically labeled ambroxol and an optional agent) can be given to a human adult in a dose of at least about 0.5-10 mg, about 1 mg, to about 15 mg., about 5 mg. to about 20 mg., at least about 25 mg, at least about 50 mg, at least about 60 mg, at least about 75 mg., at least about 100 mg, at least about 150 mg, at least about 200 mg, at least about 250 mg, at least about 300 mg, at least about 350 mg, at least about 400 mg, at least about 500 mg, at least about 750 mg at least about 1000 mg and given in one or more doses up to four or more times daily.

The form of the pharmaceutical composition of the invention such as a powder, solution, suspension etc. may be suitably selected according to the type of substance to be administered.

As an administration route, direct inhalation via the mouth using an inhaler is usually administered into the airways and in particular, directly to pulmonary tissue, the active substance contained therein produces immediate effects. Furthermore, the composition is formulated as an immediate release product, as a controlled release product or as a combination of an immediate release product in combination with a controlled release product so that therapy can begin immediately and continue over a period of time to maintain an effective concentration of active agent at the site of activity.

The following represents preferred embodiments according to the present invention:

Ambroxol Particles for Inhalation

Two main strategies are, based around particle size a) Macrophage targeting: In the case of lung infections, where, macrophage delivery of ambroxol would be optimal (such as for TB) the smallest size of ambroxol particle would be most suited in a range of 1-2 microns, as this will optimize the phagocytic process. These 1-2 micron particles could be further coated with a stabilizing coat, or a coating to enhance macrophage phagocytosis or recruitment. These 1-2 micron particles can be delivered as is by nebulization or MDL or in the case of dry powders for inhalation, may be incorporated into other particles of excipients such as leucine, by spray drying b) Lung epithelial cell targeting: to treat lung epithelial cells, much smaller ambroxol particles may be needed as these cell primary route of uptake is endocytosis, not phagocytosis as for macrophages. Therefore, ambroxol particles in the range of 0.05 to 0.2 microns are most suite, however these are too small for lung delivery themselves, and so are incorporated into either nebulized aqueous aerosols, or in spray dried engineered particles of MMAD 2-5 microns.

EXAMPLES

The Synthesis of compounds according to the present invention proceeds according to the chemical scheme which is presented in FIG. 2 hereof. In essence, 1-hydroxyl-4-amino cyclohexane of set configuration (FIG. 2) is reacted with a dibrominated-amino-benzaldehyde compound which is isotopically labeled as indicated in FIG. 2. One or both of the carbon and hydrogen substituents on the aldehyde aldehyde moiety may be isotopically labeled, depending on the isotopic substitution desired in the final isotopically labeled ambroxol, in essence, the isotopically labeled dibrominated-amino-benzaldehyde compound is condensed with 1-hydroxyl-4-amino cyclohexane to produce the isotopically labeled imine compound, which is subsequently subjected to reduction of the imine (with an optionally isotopically labeled reducing agent) to produce the isotopically labeled ambroxol compound.

Dose Response Assays

Figure 3:
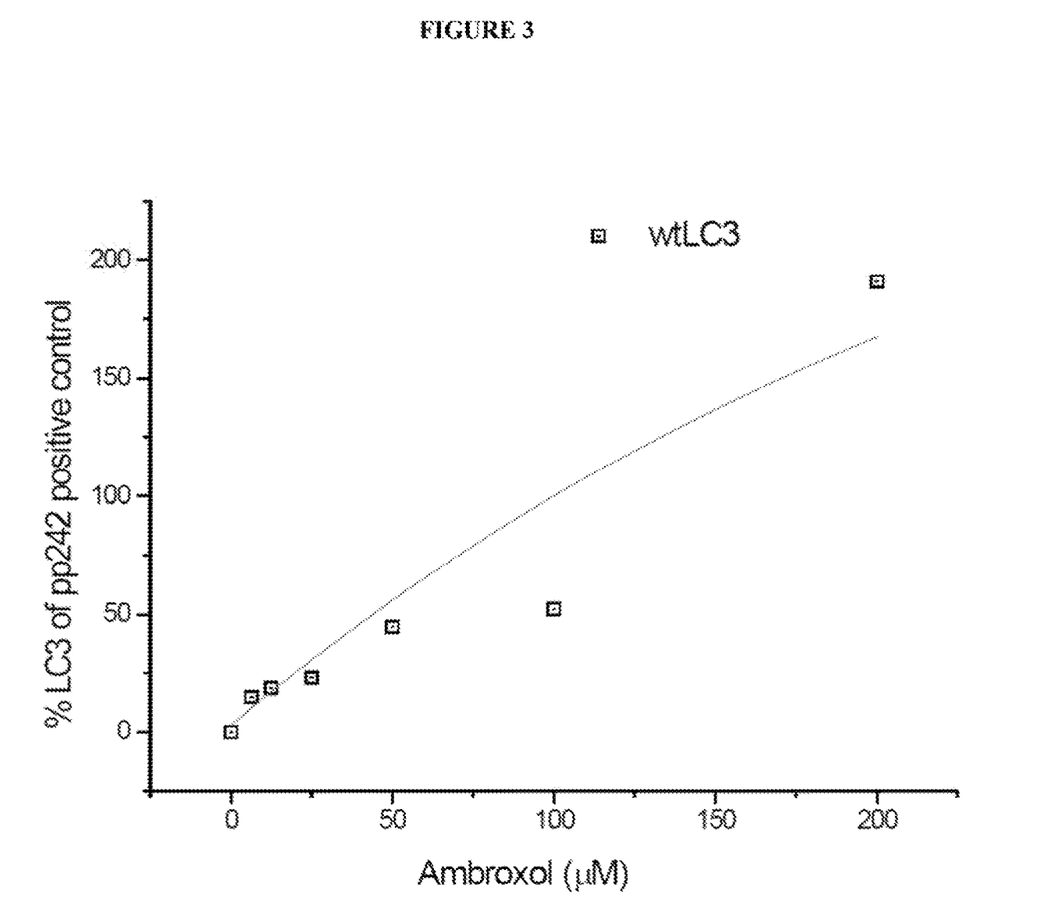
Figure 4:
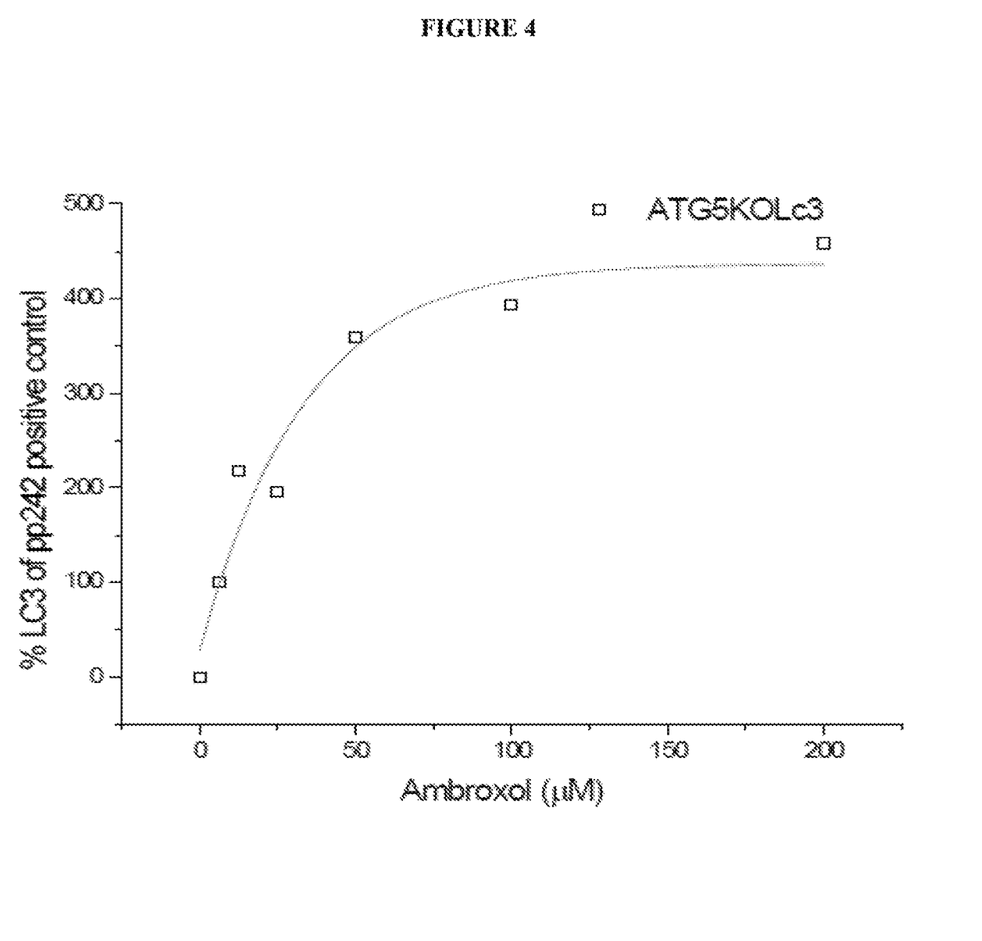
FIG. 4 shows results from the same dose response assay used to generate the data in FIG. 3, but with ATG5 knockout cells, rather than wild type cells. The data shown in this FIG. 4 evidences that even concentrations of ambroxol as low as 6.25 μM gave appreciable increases in autophagy (t test v. control p=0.0008). Again a clear dose response as observed.

Ambroxol dose response assays were conducted and the data generated is presented in the attached FIGS. 3-6. In brief, bone marrow derived macrophages from wild type and ATG5 knockouts were first studied, using a known inducer of autophagy, pp242 and LC3, puncta was quantified by Cellomics as a marker of autophagy, and the dose response of autophagy to ambroxol was determined, using pp242 induction of autophagy as 100%. The dose response of wild type cells is shown in FIG. 3: clearly even concentrations as low as 6.25 uM had a positive effect on autophagy (t test v. control p=0.025). Moreover, it is clear that across the range of ambroxol concentrations from 0 to 200 uM, higher ambroxol concentrations result in higher induction of autophagy.

The inventors next studied the same assay, described above, but in ATG5 knockout cells. The data is presented in FIG. 4. Again, even concentrations of ambroxol as low as 6.25 uM gave appreciable increases in autophagy (t test v. control p=0.0008). Again a clear dose response was observed. It is noted that the responses for ambroxol reached levels that were very much higher than pp242. One interpretation of this is that the target(s) of ambroxol induced increase in autophagy are different from the known inducer pp242.

Figure 5:
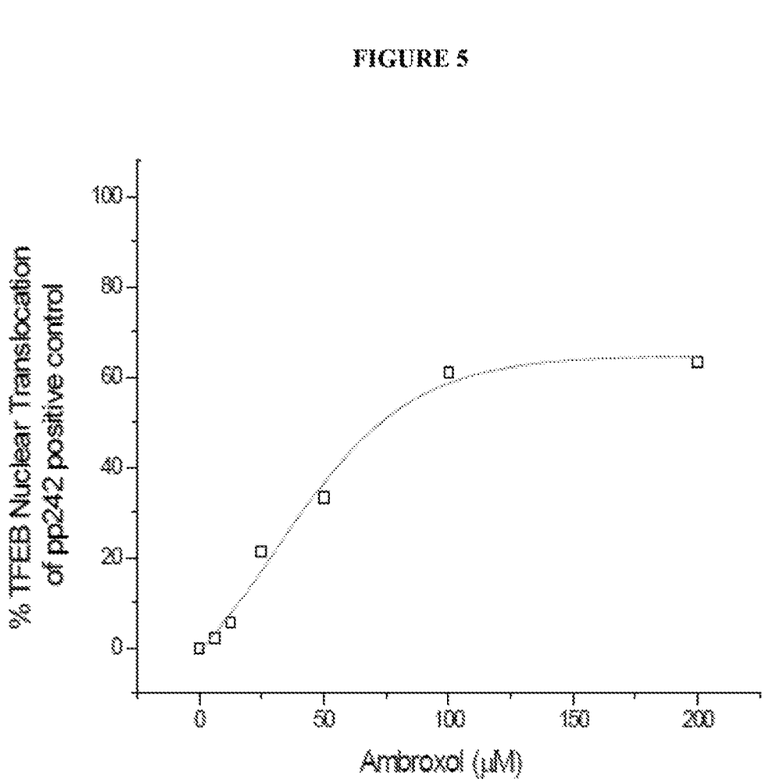
FIGS. 5 and 6 show ambroxol induction of TFEB nuclear translocation to gauge activity of ambroxol as an inducer of autophagy. A sigmoidal fit of both data sets indicated 50% of maximal autophagy induced by ambroxol was found at about 50 uM. Again significant increases were observed at 25 uM. Unlike the LC3 marker of autophagy, ambroxol always gave less effect than pp242. It is clear in all cases that increasing levels of ambroxol will increase autophagic responses.
Figure 6:
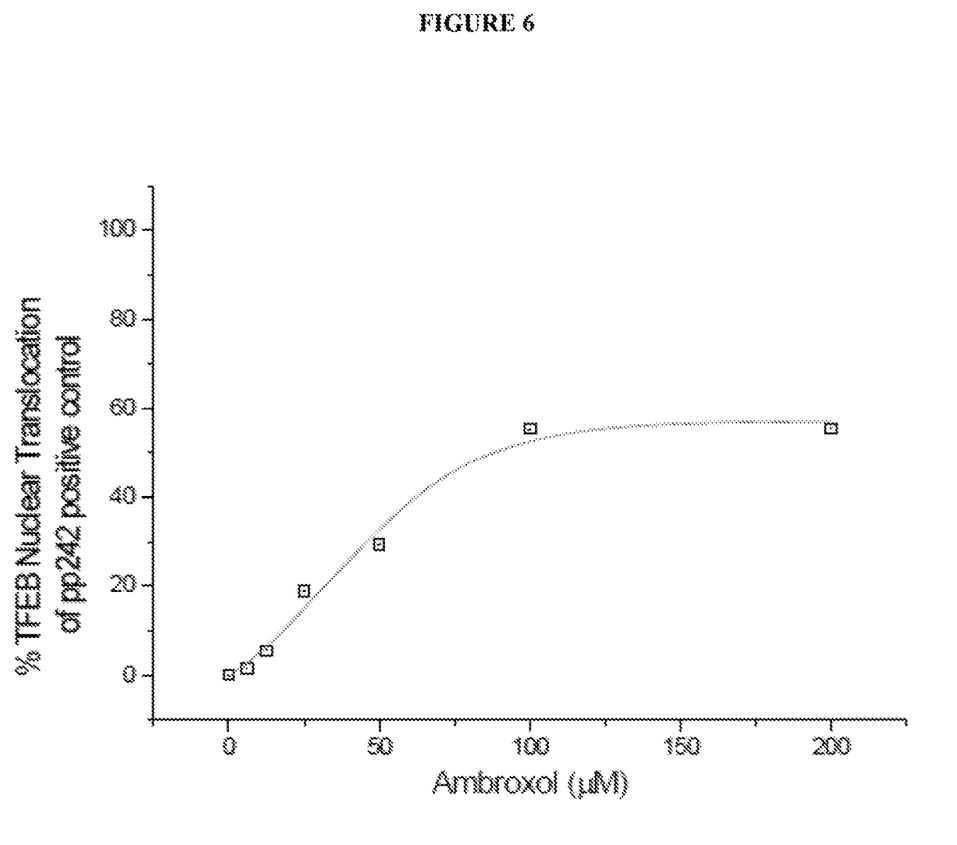

The inventors next studied ambroxol induction of TFEB nuclear translocation as above. The results from the 2 septate experiments are shown in FIGS. 5 and 6, respectively.

A sigmoidal fit of both data sets indicated 50% of maximal autophagy induced by ambroxol was found at about 50 uM.

Again significant increases were observed at 25 uM. Unlike the LC3 marker of autophagy, ambroxol always gave less effect than pp242.

From the assays performed, it is clear in all cases that increasing levels of ambroxol will increase autophagic responses.

REFERENCES

1. Vergin H, Bishop-Freudling G, Miczka M, Nitsche V, Strobel K, Matzkies F. 1984. [The pharmacokinetics and bioequivalence of various dosage forms of ambroxol]. Arzneimittel-Forschung 35:1595-1595.
2. 関隆, 松村理一郎, 公平宏 1977. A Clinico-Pharmacological Study on trans-4-(2-Amino-3, 5 dibromobenzylamino) cyclohexanol hydrochloride. 臨床薬理 8:25-31.
3. Ishiguro N, Senda C, Kishimoto W, Sakai K, Funae Y, Igarashir 2000, Identification of CYP3A4 as the predominant isoform responsible for the metabolism of ambroxol in human liver microsomes. Xenobiotica 30:71-80.
4. Anttila S, Hukkanen J, Hakkola J, Stjernvall T, Beaune P, Edwards R J, Boobis A R, Pelkonen O, Raunio H. 1997. Expression and localization of CYP3A4 and CYP3A5 in human lung. American journal of respiratory cell and molecular biology 16:242-249.

We claim:

1. A method of treating an autophagy-mediated disease state or condition in a patient or subject in need comprising administering to said patient or subject an effective amount of a compound according to the chemical structure:

or
   a pharmaceutically acceptable salt, enantiomer, diastereomer, or solvate thereof.

2. A method of treating an autophagy-mediated disease state or condition in a patient or subject in need comprising administering to said patient or subject an effective amount of a composition comprising an effective amount of a compound according to the chemical structure or a pharmaceutically acceptable salt, enantiomer, diastereomer, or solvate thereof.

3. The method according to claim 1 wherein said autophagy-mediated disease state or condition is a lung disease or condition.

4. The method according to claim 3 wherein said lung disease or condition is a *Mycobacterium* infection, Chronic Obstructive Pulmonary Disease (COPD), asthma, pulmonary fibrosis, cystic fibrosis, Sjogren's disease, a viral infection or lung cancer.

5. The method according to claim 3 wherein said lung disease or condition is *Mycobacterium tuberculosis.*

6. The method according to claim 3 wherein said lung disease or condition is *Mycobacterium kansasii, Mycobacterium avium* or *Microbacterium abscessus.*

7. The method according to claim 3 wherein said lung disease or condition is an infection caused by methicillin resistant *Staphylococcus aureus* (MRSA), *Acinetobacter baumannii* or inhalation anthrax.

8. The method according to claim 3 wherein said lung disease or condition is COPD.

9. The method according to claim 3 wherein said lung disease or condition is asthma.

10. The method according to claim 3 wherein said lung disease or condition is cystic fibrosis.

11. The method according to claim 3 wherein said lung disease or condition is Sjogren's disease.

12. The method according to claim 3 wherein said lung disease or condition is lung cancer.

13. The method according to claim 12 wherein said lung cancer is small cell lung cancer.

14. The method according to claim 12 wherein said lung cancer is non-small cell lung cancer.

* * * * *